(12) United States Patent
Shaw

(10) Patent No.: US 11,236,056 B2
(45) Date of Patent: Feb. 1, 2022

(54) SMALL MOLECULES AND METHODS OF REDUCING INJURIES CAUSED BY RADIATION OR CHEMICALS

(71) Applicant: Jiajiu Shaw, Henderson, NV (US)

(72) Inventor: Jiajiu Shaw, Henderson, NV (US)

(73) Assignee: 21ST CENTURY THERAPEUTICS, INC., Detroit, MI (US)

( * ) Notice: Subject to any disclaimer, the term of this patent is extended or adjusted under 35 U.S.C. 154(b) by 0 days.

(21) Appl. No.: 16/992,681

(22) Filed: Aug. 13, 2020

(65) Prior Publication Data

US 2021/0087153 A1    Mar. 25, 2021

Related U.S. Application Data

(60) Provisional application No. 62/903,032, filed on Sep. 20, 2019.

(51) Int. Cl.
*C07D 261/18* (2006.01)
*A61P 39/00* (2006.01)

(52) U.S. Cl.
CPC .......... *C07D 261/18* (2013.01); *A61P 39/00* (2018.01)

(58) Field of Classification Search
CPC ................................ C07D 261/18; A61P 39/00
See application file for complete search history.

(56) References Cited

FOREIGN PATENT DOCUMENTS

CA          1134837    * 11/1982    ........... C07D 261/02

OTHER PUBLICATIONS

STN Registry database entry for CAS RN 222801-39-4, entry date Jun. 28, 2018; Accessed Jul. 29, 2021.*

STN Registry database entry for CAS RN 1247403-64-0, entry date of Oct. 27, 2010; Accessed Jul. 29, 2021.*

Comparison of Two Molecular Scaffolds, 5-Methylisoxazole-3-Carboxamide and 5-Methylisoxazole-4-Carboxamide., Y. Song et al., Current Pharmaceutical, 2014, pp. 146-152.

Chemosenstizing Effects of a Novel Anti-inflammatory Small Molecule, UTL-5g and Its Analogs, B. Chen et al., American Journal of Biomedical Sciences, 2015, 7(3), pp. 190-197.

The Small-molecule TNF-α Modulator, UTL-5g, Reduces Side Effects Induced by Cisplatin and Enhances the Therapeutic Effect of Cisplatin in vivo, J. Shaw et al. Journal of Experimental Therapeutics and Oncology, vol. 9. pp. 129-137, 2011.

* cited by examiner

*Primary Examiner* — Alicia L Otton

(57) ABSTRACT

A series of small molecule, radioprotective agents based on a compound of the general formula (I):

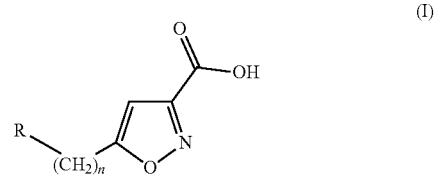

or pharmaceutically acceptable salts thereof, wherein n is 1 or 2, and, independently, R is Br, Cl, H—O, $H_3C$—S,

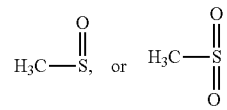

and use of the compounds to protect healthy tissue/organs of subjects to reduce the injuries caused by radiation or chemicals.

15 Claims, 5 Drawing Sheets

Amifostine (WR-2721)

WR-3689

Cystaminum (Cystamine)

2-pyridinemethanethiol 2-(methylsulfinyl)ethylamine

Recilisib tempol (4-hydroxy-2,2,6,6,tetramethylpiperidine-1-oxyl)

SMALL MOLECULES AND METHODS OF REDUCING INJURIES CAUSED BY RADIATION OR CHEMICALS

RELATED APPLICATION

The application is based on U.S. provisional application Ser. No. 62/903,032, filed Sep. 20, 2019 to which priority is claimed under 35 U.S.C. § 120 and of which the entire specification is hereby expressly incorporated by reference.

FIELD OF INVENTION

The present invention relates generally to a series of new compounds and methods of reducing injuries caused by radiation or chemicals.

BACKGROUND OF INVENTION

There are generally two types of total-body irradiation (TBI). One type of TBI is used in conjunction with bone marrow transplantation as a medical treatment for cancer patients. In such cases, TBI is often used together with high dose chemotherapy to kill leukemia, lymphoma, and/or myeloma cells in bone marrow. In this type of medical procedure, TBI treatment can involve 1 or 2 treatments per day for up to several days. In this case, TBI is done in a controlled manner for the benefit of cancer patients.

Another type of TBI occurs when people are exposed to radiation during a nuclear attack or when a dirty bomb is used by terrorists or accidental exposure. In such cases, people affected by the TBI are likely to suffer certain injuries and may die. Using physical barriers to block the radiation is one countermeasure. However, many times, it is not practical or possible to use a physical barrier. Therefore, it is very important to use chemical agents to reduce the negative effects that radiation has on normal tissues/organs and/or to increase the chance of survival.

In addition to TBI, localized radiation can be applied to living organisms.

Generally, localized radiation exposure is used for medical purposes. More specifically, when localized radiation is applied to certain parts of a patient's body, it is usually for cancer treatment. Nevertheless, in treating cancer patients, localized irradiation, may also induce adverse side effects to nearby or adjacent healthy living tissues/organs.

Currently, there are only a few pharmaceutical agents that have been approved to reduce radiation-induced side effects.

As of Mar. 29, 2018, there were three medical countermeasure (MCM) products that were FDA-approved to increase survival in patients exposed to myelosuppressive doses of radiation. These three products, that may be used to treat adult and pediatric patients acutely exposed to myelosuppressive doses of radiation, a condition known as hematopoietic symptoms of acute radiation syndrome (H-ARS), are listed below:

Neupogen (filgrastim)—approved March 2015
Neulasta (pegfilgrastim)—approved November 2015
Leukine (sargramostim)—approved Mar. 29, 2018

All three of these approved products are biologics (i.e., large-molecule protein drugs). Biologics have advantages but also disadvantages as compared to small-molecule drugs. In general, some of the advantages of small molecules as compared to biologics, include their stability, easy to synthesize, cost to produce, ease to administer, etc. As discussed below, the present invention is directed to small-molecule radioprotectors.

In the field of small molecules, radioprotective agents can be categorized into two main classes that are briefly described below:

A. Thio Compounds

Amifostine

Amifostine is a well-known broad-spectrum radioprotector that has been used to reduce the adverse side effects induced by DNA-damaging radiotherapy and DNA-binding chemotherapeutic agents including platinum drugs (e.g. cisplatin) for a number of years. Unfortunately, amifostine has several shortcomings. Treatment with amifostine can result in nausea, vomiting, diarrhea, and transit hypotension (Mabro et al., *A Risk-Benefit Assessment of Amifostine in Cytoprotection*, Drug Saf., 21, (5), 367-87 (1999)). While the use of amifostine is becoming more widespread, an increased number of cutaneous reactions have also been reported (Demiral et al., *Amifostine-Induced Toxic Epidermal Necrolysis During Radiotherapy: A Case Report.*, Jpn. J. Clin. Oncol., 32, (11), 477-9 (2002)).

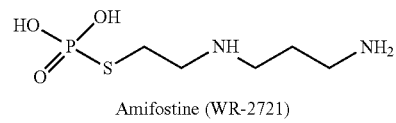 [SMILES: NCCCNCCSP(=O)(O)O]

Amifostine (WR-2721)

Based upon these studies, amifostine does not appear to be an ideal radioprotector.

WR-3689

WR-3689 or S-2-(3-methylaminopropylamino)ethylphosphorothioic acid (FIG. 1), was reported to be effective in radioprotection. WR-3689 showed protection against gamma-ray-induced intestinal damage (Murray, D., et al., *Protection by WR-3689 against Gamma-Ray-Induced Intestinal Damage: Comparative Effect on Clonogenic Cell Survival, Mouse Survival, and DNA Damage*. Radiat Res, 1989. 120(2): p. 339-51).

Cystamine

Cystaminum (cystamine) was approved in Russia as a radioprotector. Cystaminum is injected 10-30 min before radiotherapy and the protective effect lasts about 5 hours.

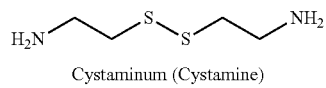

Cystaminum (Cystamine)

Other Thio Compounds

In addition, a number of pyridine and pyrimidine compounds containing sulfur side-groups have been investigated as potential radioprotectors. For example, 2-pyridinemethanethiol has been studied as a potential radioprotector, but needs further study (Barnes et al., *N-Heterocyclic Compounds as Radioprotectors 1,2-Pyridinemethanethiol, 2-Pyrazinemethanethiol and Related Compounds*, European Journal of Medicinal Chemistry—Chimica Therapeutica, 18(6), 515-519, 1983).

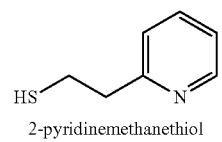

2-pyridinemethanethiol

Recilisib is a newer thiol compound (marketed as Ex-Rads by Onconova Therapeutics). In cell and animal models, Ex-RAD has been shown to protect hematopoietic and gastrointestinal tissues from radiation injury when given either before or after exposure (Ann M Thayer, The Drug that may Never be Used, C&EN, 90, 26, 23-26. https://cen.acs.org/articles/90/i26/Drugs-Never-Used.html (Jun. 25, 2012)).

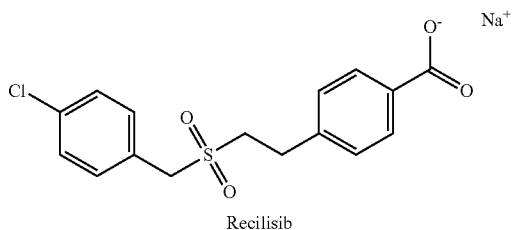 [SMILES: [Na+] ; O=C([O-])c1ccc(CCS(=O)(=O)Cc2ccc(Cl)cc2)cc1]

Recilisib

B. Nitroxides

Nitroxides may be the second most promising group of compounds for use as potential small-molecule radioprotectors, some of which are in clinical development. Currently, the most advanced nitroxide radioprotector under development is tempol (4-hydroxy-2,2,6,6-tetramethylpiperidine-1-oxyl) (Hahn et al., *Tempol, a Stable Free Radical, is a Novel Murine Radiation Protector*, Cancer Res. 1; 52(7):1750-30 Apr. 1992).

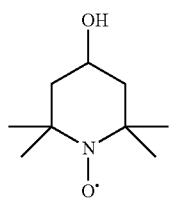

tempol (4-hydroxy-2,2,6,6,tetramethylpiperidine-1-oxyl)

Overall, the most notable broad-spectrum radioprotector is amifostine. Amifostine can be used as a radioprotector, which is administered before radiation exposure. As mentioned above, treatment with amifostine can result in nausea, vomiting, diarrhea, and transit hypotension. In addition, amifostine needs to be administered by infusion, which can be inconvenient for many patients.

Other than the broad-spectrum radioprotectors, there are several small-molecule radioprotectors that provide protection against specific side effects induced by radiation or radiotherapy. One such example is potassium iodide, KI. KI can provide important protection for the thyroid gland from radiation. However, KI doesn't have any effect in protecting other organs from radiation. In addition, KI can cause several adverse effects, including skin rashes, swelling of the salivary glands, and allergic reactions.

In general, broad-spectrum radioprotectors are more useful than narrow-spectrum radioprotectors because they protect more organs/tissues and increase survival rates for those being treated. However, broad-spectrum radioprotectors that are effective against radiation or radiotherapy are scarce. Therefore, there is an imminent need to discover and/or develop such radioprotectors.

UTL-5g described in U.S. Pat. No. 6,727,272, has been shown to protect liver, kidney, platelets, and/or lung from localized radiation and chemotherapeutic agents (Shaw et al, *The Small-Molecule TNF-α Modulator, UTL-5g, Reduces Side Effects Induced by Cisplatin and Enhances the Therapeutic Effect of Cisplatin In Vivo*, Journal of Experimental Therapeutics and Oncology, Vol. 9, pp. 129-137; Shaw et al., *Pretreatment with A Small-Molecule Tumor Necrosis Factor-Alpha (TNF-α) Inhibitor, UTL-5g, Reduced Radiation-Induced Acute Liver Toxicity in Mice*, Am. J. Biomed. Sci. 4(2), 123-131 (2012); and Brown et al., *UTL-5g Lowers Levels of TGF-β and TNF-α Elevated by Lung Irradiation and Does Not Affect Tumor-response to Irradiation*, Am. J. Biomed. Sci., 6(3), 157-165 (2014)).

UTL-5g was also found to increase the survival rates of mice treated with chemotherapeutic agents or lipopolysaccharide (LPS) (Shaw et al., *The Small-Molecule TNF-α Inhibitor, UTL-5g, Delays Deaths and Increases Survival Rates for Mice Treated with High Doses of Cisplatin*, Cancer Chemother Pharmacol, 72:703-707 (2013); and Zhang et al., *UTL-5g Lowers Elevated Blood Levels of TNF-α and TGF-β and Increases Survival Rates in Animals Treated with LPS/D-(+)-Galactosamine*, Am. J. Biomed. Sci. 6(2), 128-138 (2014)).

Further, the active metabolite of UTL-5g was identified and has been shown to be anti-inflammatory and anti-arthritic (Zhang et al., *UTL-5g Lowers Elevated Blood Levels of TNF-α and TGF-β and Increases Survival Rates in Animals Treated with LPS/D-(+)-Galactosamine*, Am. J. Biomed. Sci. 6(2), 128-138 (2014); Song et al., *Comparison of Two Molecular Scaffolds, 5-Methylisoxazole-3-Carboxamide and 5-Methylisoxazole-4-Carboxamide*, Current Pharmaceutical Design, 2014, 20, 146-152; and Shaw et al., *A Liquid Chromatography with Tandem Mass Spectrometry Method for Simultaneous Determination of UTL-5g and its Metabolites in Human Plasma*, Journal of Chromatography B, 991 (2015) 92-98).

Recently, the present inventor has conducted further research in the area of radioprotection and have more discoveries, including the series of new chemical entities and methods of reducing adverse effects induced by radiation or chemicals which are the subject matter of the present invention.

Compared with all known small-molecule medical countermeasures, the series of small-molecule radioprotectors disclosed in the present invention have molecular structures significantly different from all presently known radioprotectors. Thus, the new compounds disclosed herein by the inventor and the use of these compounds as medical countermeasures provide a significant advance in the field of radioprotectors.

BRIEF SUMMARY OF THE INVENTION

According to various features, characteristics and embodiments of the present invention which will become apparent as the description thereof proceeds, the present invention provides a compound of formula (I)

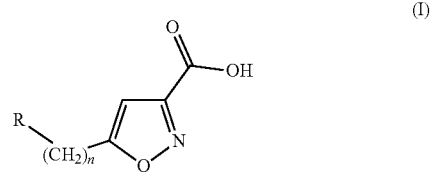

or pharmaceutically acceptable salt thereof, wherein n is 1 or 2, and, independently, R is Br, Cl, H—O, H₃C—S,

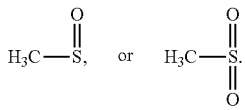

The present invention also provides a pharmaceutical composition comprising a compound or pharmaceutically acceptable salt of formula (I).

The present invention further provides a method of protecting healthy living tissues/organs of a subject from radiation- or chemical-induced injuries which method comprises administration of a pharmaceutical composition comprising a compound or pharmaceutically acceptable salt of formula (I).

BRIEF DESCRIPTION OF THE DRAWINGS

The present invention will be described with reference to the attached drawings which are given as non-limiting examples only, in which.

DETAILED DESCRIPTION OF THE INVENTION

Figure 1:
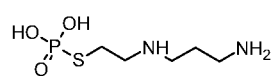
FIG. 1 depicts structure of some representative radioprotective agents.
Figure 1:
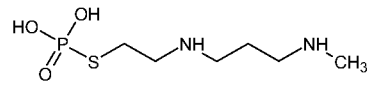
Figure 1:
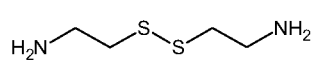
Figure 1:
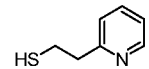
Figure 1:
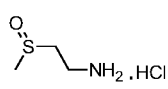
Figure 1:
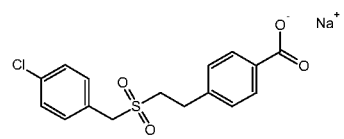
Figure 1:
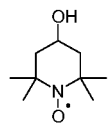

The series of small-molecule radioprotectors disclosed in the present invention are based on a compound of general formula (I):

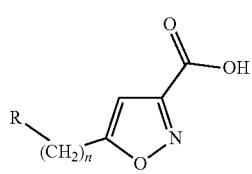

(I)

or pharmaceutically acceptable salts thereof, wherein n is 1 or 2, and, independently, R is Br, Cl, H—O, H₃C—S,

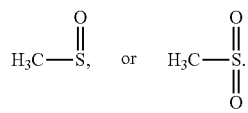

Representative compounds include:

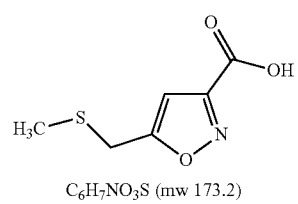

(UTS-1401)

C₆H₇NO₃S (mw 173.2)

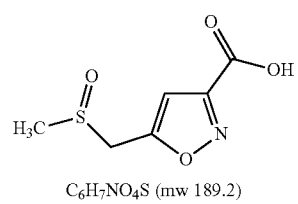

(UTS-1402)

C₆H₇NO₄S (mw 189.2)

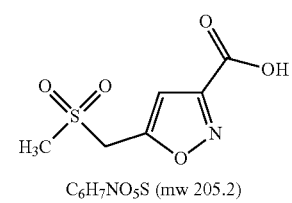

(UTS-1403)

C₆H₇NO₅S (mw 205.2)

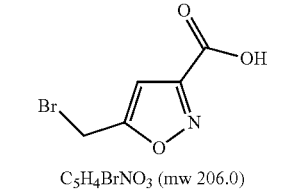

C₅H₄BrNO₃ (mw 206.0)

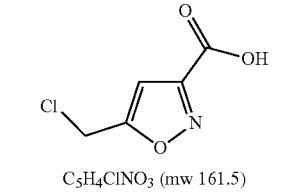

C₅H₄ClNO₃ (mw 161.5)

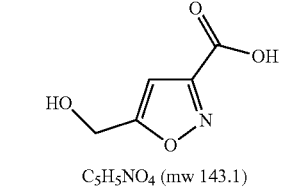

C₅H₅NO₄ (mw 143.1)

The present invention also provides pharmaceutical compositions that comprise an effective amount of at least one compound of the formula (I) and/or pharmaceutically acceptable salt thereof, and pharmaceutically suitable excipients.

Examples of suitable forms of such pharmaceutical compositions include tablets, coated tablets, solutions, suspensions, emulsions, powders, granules, capsules, creams, lotions, suppositories, transdermal patches, and syrups. For example, a simple pharmaceutical composition may be made by dissolving 500 mg of UTS-1403 in 100 mL of saline and sterilizing the solution.

The present invention also provides a method of protecting normal tissues/organs from radiation-induced injuries, in which method a person subject to radiotherapy or accidental radiation exposure is administered an effective amount of the pharmaceutical compositions of the present invention.

The present invention also provides a method of protecting a subject from radiation-induced injuries (including tissue/organ injuries and death) by administration of the pharmaceutical compositions of the present invention, wherein the radiation-induced injuries are induced by total-body irradiation or localized radiotherapy; said localized radiotherapy may be applied to a cancer patient for treatment purpose and said total-body irradiation may be applied to a patient for therapeutic purpose or applied to a subject exposed to non-medical radiation resulted from terrorism, nuclear war or accidental exposure.

The present invention further provides a method of protecting a subject from chemical-induced injuries (including tissue/organ injuries and death) by administration of the pharmaceutical compositions of the present invention, wherein the chemical-induced injuries are induced by chemotherapy or by accidental chemical exposure.

Features and characteristics of the present invention will be exemplified by the following examples which are provided as non-limiting examples only.

Example 1

Syntheses of UTS-1401, -1402, -1403, and Related Compounds
Synthesis of Intermediate Compound 2

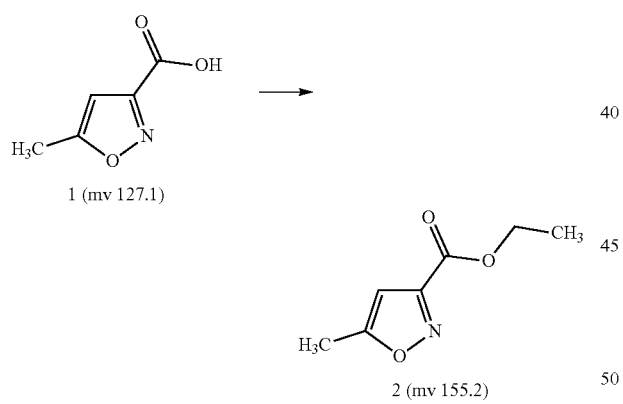

Procedure:

In a 250 mL round bottom flask, 5-methylisoxazole-3-carboxylic acid (1) (17.0 g, 133.8 mmol) was suspended in ethanol (170 mL) and conc. $H_2SO_4$ (17 mL) was added drop-wise.

The reaction mixture was heated at 80° C. for 2 h and completion of the reaction was monitored by TLC using Ethyl acetate:Hexane (5:5) as a mobile phase.

The reaction mixture was concentrated under reduced pressure and diluted with $H_2O$ (250 mL) and extracted with ethyl acetate (3×250 mL). The organic layers were separated, combined, dried (by $Na_2SO_4$) and concentrated under reduced pressure to yield a crude intermediate product. The crude intermediate product (2) was purified by column chromatography (13% ethyl acetate in hexanes), yield 88%.

Synthesis of Intermediate Compound 3

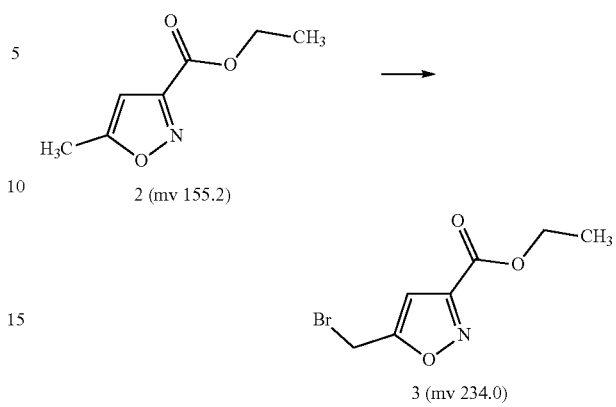

Procedure:

In a 100 mL round bottom flask, intermediate compound (2) (2.5 g, 16.11 mmol) was suspended in $CCl_4$ (30 mL). Benzoyl peroxide (BPO) (585 mg, 2.41 mmol) and N-bromosuccinimide (NBS) (2.86 g, 19.33 mmol) were then added. The reaction mixture was stirred for 16 h at 95° C. and the completion of the reaction was monitored by LC/MS.

The reaction mixture was concentrated under reduced pressure to yield a crude intermediate product. The crude intermediate product (3) was purified by flash chromatography (2% ethyl acetate in hexanes), yield 51%.

Synthesis of Intermediate Compound 4

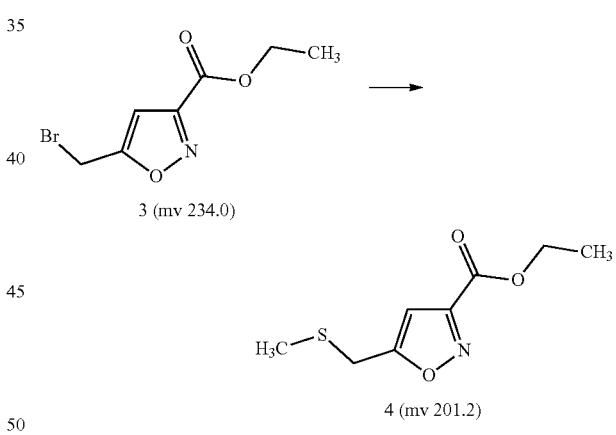

Procedure:

In a 50 mL one neck round bottom flask, intermediate compound (3) (3.0 g, 12.81 mmol) was suspended in DMF (30 mL) under nitrogen and the reaction mixture was cooled to 10° C. using ice bath. Sodium thiomethoxide (0.89 g, 12.81 mmol) was added in portions. After completion of addition, ice bath was removed and the reaction mixture was allowed to warm to room temperature and stirred for 30 min. The completion of the reaction was monitored by LC/MS.

After completion of the reaction, the reaction mixture was diluted with $H_2O$ (200 mL) and then extracted with Ethyl acetate (3×200 mL). The organic layers were separated, combined and dried (by $Na_2SO_4$), concentrated to yield a crude intermediate product. The crude intermediate product (4) was purified by flash chromatography (2% ethyl acetate in hexane), yield 62%.

Synthesis of UTS-1401

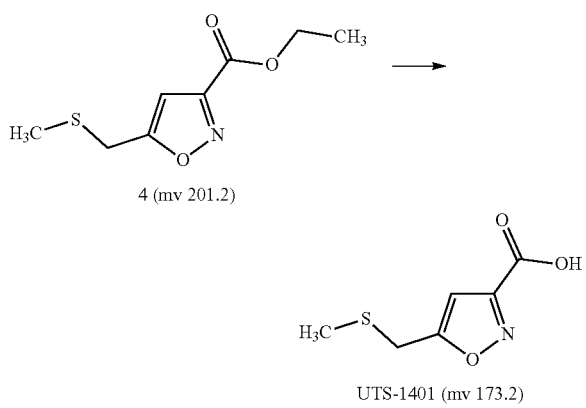

Procedure:

In a 50 mL one neck round bottom flask, intermediate compound (4) (1.4 g, 6.96 mmol) was suspended in THF (10 mL) and reaction mixture was cooled at 10° C. and LiOH (1.16 g, 27.82 mole) in H$_2$O (10 mL) was added drop-wise. The reaction mixture was stirred at same temperature for 45 min. The completion of the reaction was monitored by TLC using Methanol: DCM (1:9) as a mobile phase.

After completion of the reaction, the reaction mixture was concentrated under reduced pressure and then washed with diethyl ether (2×20 mL). The aqueous layer was cooled to 5° C.-10° C. and acidified with dilute HCl (~5.0 mL) and then extracted with 15% ethyl acetate:methanol (3×150 mL). The organic layer was separated, dried (by Na$_2$SO$_4$) and concentrated to yield a crude product. The crude product (UTS-1401) was purified by trituration using pentane, yield 92%.

Mass 174 (M+). $^1$H NMR, 400 mHz, DMSO-d$_6$, δ(ppm): 2.09 (3H, s, CH$_3$), 2.50, 3.95 (2H, s, CH$_2$), 6.71 (1H, s, C=CH), 14.04 (1H, s, OH).

Synthesis of Intermediate Compound 6

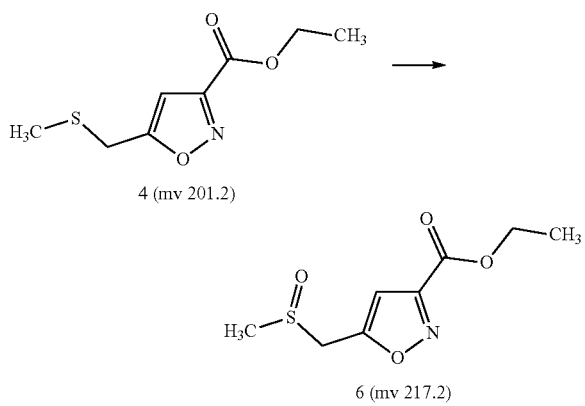

Procedure:

To a 100 mL three neck round bottom flask, intermediate compound (4) (1.75 g, 8.69 mmol) was suspended in DCM (30 mL) and reaction mixture was cool at −78° C. Then meta-chloroperoxybenzoic acid (m-CPBA) (1.65 g, 9.56 mmol) in DCM (30 mL) was added drop-wise to it at the same temperature. The reaction mixture was stirred at same temperature for 1 h. Then reaction mixture was allowed to come to room temperature for 1 h. The completion of the reaction was monitored by TLC using Methanol: DCM (1:9) as a mobile phase.

After completion of the reaction, the reaction mixture was neutralized with saturated NaHCO$_3$ solution and then extracted with DCM (2×20 mL). The organic layer was separated, dried (by Na$_2$SO$_4$) and concentrated to yield a crude intermediate product. The crude intermediate product (6) was purified by Flash chromatography (8% Methanol in DCM), yield 80%.

Synthesis of UTS-1402

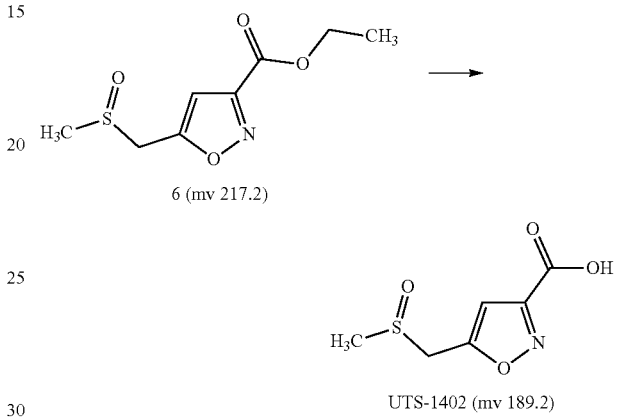

Procedure:

To a 50 mL one neck round bottom flask, intermediate compound (6) (1.5 g, 6.91 mmol) was suspended in THF (10 mL) and reaction mixture was cool at 10° C. and LiOH (1.15 g, 27.64 mmol) in H$_2$O (10 mL) was added drop-wise to it. The reaction mixture was stirred at same temperature for 45 mins. The completion of the reaction was monitored by TLC using Methanol: DCM (1:9) as a mobile phase.

After completion of the reaction, the reaction mixture was concentrated under reduced pressure and then washed with diethyl ether (2×20 mL). The aqueous layer was cooled at 5° C.-10° C. and acidified it with dil. HCl (~5.0 mL) and then extracted it with 15% ethyl acetate:methanol (3×150 mL). The organic layer was separated, dried over anhydrous sodium sulphate and concentrated to yield a crude product. The crude product (UTS-1402) was purified by trituration using pentane, yield 62%.

Mass 190 (M+). $^1$H NMR, 400 mHz, DMSO-d$_6$, δ(ppm): 2.60 (3H, d, CH$_3$), 4.40 (2H, q, CH$_2$), 6.83 (1H, s, C=CH), 14.11 (1H, s, OH).

Synthesis of intermediate compound 5

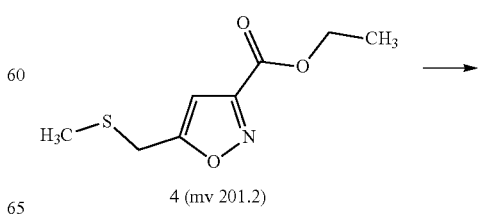

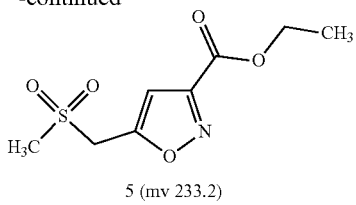

5 (mw 233.2)

Procedure:

To a 100 mL three neck round bottom flask, intermediate compound (4) (1.00 g, 4.97 mmol) was suspended in DCM (15 mL) and reaction mixture was cool at 0° C. and m-CPBA (2.1 g, 12.42 mmol) in DCM (15 mL) was added drop-wise to it at the same temperature. The reaction mixture was stirred at same temperature for 30 min. Then reaction mixture was allowed to come to room temperature and stirred for 1 h. The completion of the reaction was monitored by TLC using Ethyl acetate: Hexane (5:5) as a mobile phase.

After completion of the reaction, the reaction mixture was neutralized with satd. NaHCO$_3$ solution and then extracted with DCM (2×50 mL). The organic layer was separated, dried (by Na$_2$SO$_4$) and concentrated to yield a crude intermediate product. The crude intermediate product (5) was purified by flash chromatography (15% Ethyl acetate in Hexane), yield 82%.

Synthesis of UTS-1403

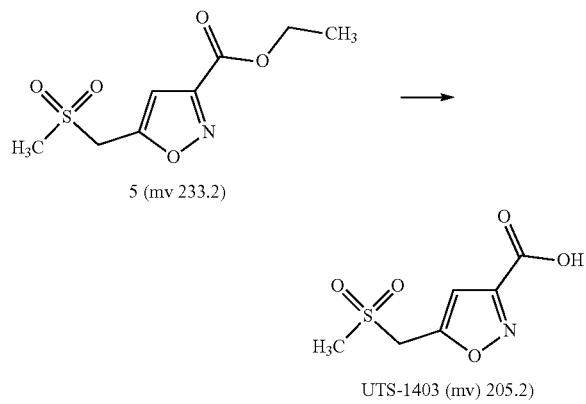

Procedure:

In a 50 mL one neck round bottom flask, intermediate compound 5 (0.95 g, 4.05 mmol) was suspended in THF (10 mL) and reaction mixture was cooled at 10° C. and LiOH (0.68 g, 16.23 mole) in H$_2$O (10 mL) was added drop-wise. The reaction mixture was stirred at same temperature for 45 min. The completion of the reaction was monitored by TLC using methanol:DCM (1:9) as a mobile phase.

After completion of the reaction, the reaction mixture was concentrated under reduced pressure and then washed with diethyl ether (2×20 mL). The aqueous layer was cooled at 5° C.-10° C. and acidified it with dil. HCl (~5.0 mL). Aqueous layer was then extracted with 15% ethyl acetate: methanol (3×150 mL). The organic layer was separated, dried (by Na$_2$SO$_4$) and concentrated to yield a crude product. The crude product (UTS-1403) was purified by trituration using pentane, yield 75%.

Mass 206 (M+), $^1$H NMR, 400 mHz, DMSO-d$_6$, δ(ppm): 3.15 (3H, q, CH$_3$), 5.02 (2H, q, CH$_2$), 6.92 (1H, s, C=CH), 14.19 (1H, s, OH).

Example 2

Radioprotection by UTS-1401, -1402, and -1403 (30 Min Pretreatment)

NIH-Swiss female mice were divided into 5 groups (8 mice/group). Thirty min prior to 7.5 Gy TBI, mice were treated by i.p. injection with UTS-1401, -1402, and -1403 (80 mg/kg each) or vehicle, respectively. Mice in control group were not irradiated. Definition of "death" used in this study was when a mouse actually died or when a mouse lost 20% or more of its bodyweight. The result of this study showed that pretreatment of all 3 UTS compounds increased the survival of irradiated mice.

Figure 2:
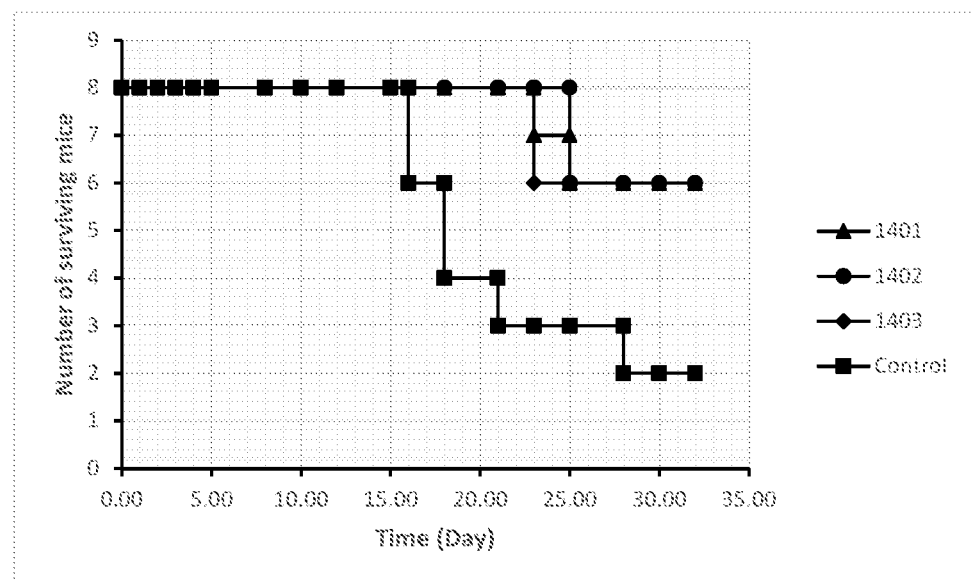
FIG. 2 is a graph of radioprotection by UTS-1401, -1402, and -1403, (30 min before TBI) on TBI induced mortality in NIH Swiss female mice.

FIG. 2 is a graph of the radioprotection of UTS-1401, -1402, and -1403 determined according to Example 2.

Example 3

Drug Dose-Dependent Radioprotection of UTS-1401 (30 Min Pretreatment)

NIH-Swiss female mice were divided into 4 groups (8 mice/group). Thirty min prior to 7.5 Gy TBI, mice were treated by i.p. injection with UTS-1401 (0, 2, or 6 mg/mL or 0, 25, or 75 mg/kg) or vehicle, respectively. Mice in control group were not irradiated. Definition of "death" used in this study was when a mouse actually died or when a mouse lost 20% or more of its bodyweight. The result of this study showed that pretreatment of UTS-1401 before TBI increased the survival rate of mice in a dose-dependent manner.

Figure 3:
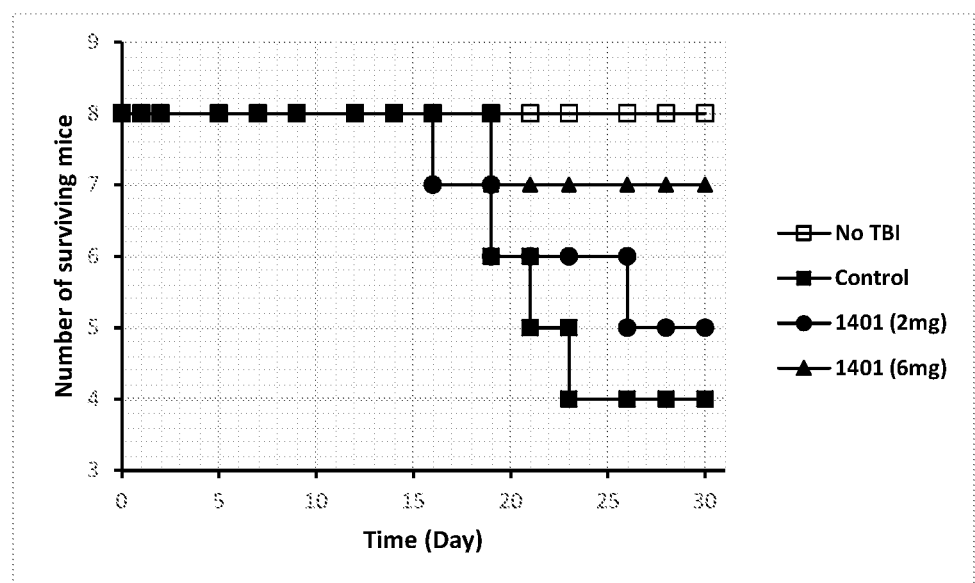
FIG. 3 is a graph of drug dose-dependent radioprotection of UTS-1401 (30 min before TBI) on TBI induced mortality in NIH-Swiss female mice.

FIG. 3 is a graph of the dose-dependent effect of UTS-1401 on TBI induced mortality in NIH-Swiss mice determined according to Example 3.

Example 4

Radioprotection of UTS-1401 as Compared with Amifostine

NIH-Swiss female mice were divided into 8 groups (10 mice/group). (A) Forty-five min prior to 7.5 Gy TBI, mice were treated by i.p. injection with UTS-1401 (75 mg/kg), amifostine (75 mg/kg) or vehicle, respectively. Mice in control group were not irradiated. (B) Same procedure as in (A) except that mice were treated by testing agents forty-five min after 7.5 Gy TBI. The results showed that (1) UTS-1401 and amifostine increased the survival rate of mice whether it was administered 45 min before or after TBI, but UTS-1401 showed better radioprotection as compared with amifostine, and (2) UTS-1401 significantly increased the survival rate of mice when it was administered 45 min after TBI, but amifostine did not increase the survival rate.

Figure 4:
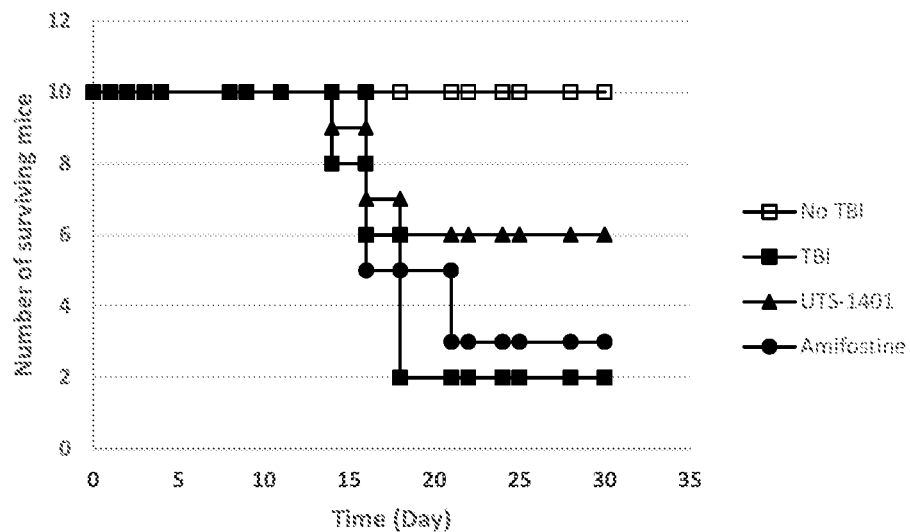
FIG. 4 is a graph of the effects of UTS-1401 and amifostine (administered 45 minutes before TBI) on TBI induced mortality in NIH-Swiss female mice.

FIG. 4 is a graph of the effects of UTS-1401 and amifostine on TBI induced in NIH-Swiss mice mortality administered 45 minutes before TBI determined according to Example 4.

Figure 5:
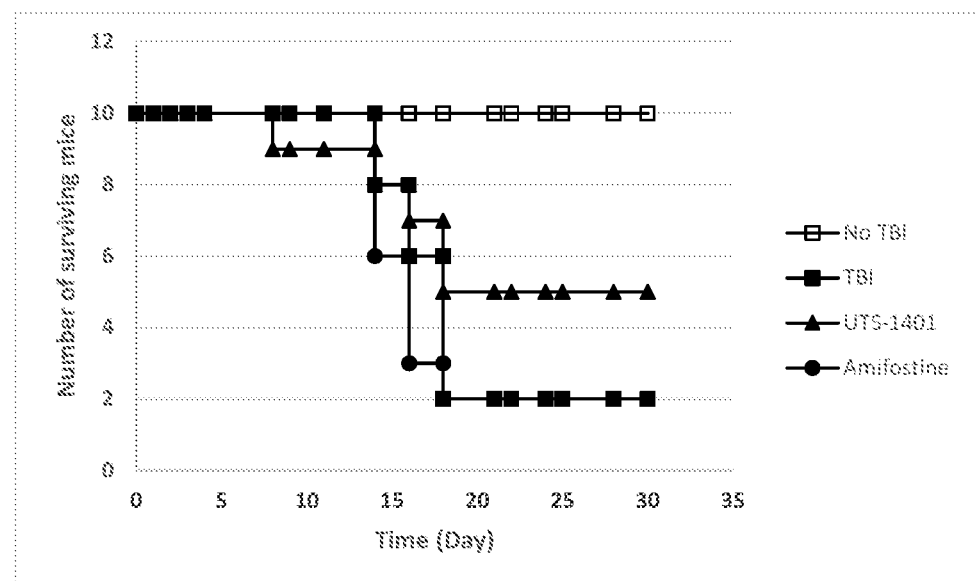
FIG. 5 is a graph of the effect of UTS-1401 and amifostine (administered 45 minutes after TBI) on TBI induced mortality in NIH-Swiss female mice.

FIG. 5 is a graph of the effects of UTS-1401 and amifostine on TBI induced in NIH-Swiss mice mortality administered 45 minutes after TBI determined according to Example 4.

Example 5

Radioprotection of UTS-1401 (24 hr Pretreatment)
For NIH Swiss Male Mice

NIH Swiss male mice were studied for the radioprotective effects of UTS-1401 at 50, 100, and 150 mg/kg respectively by i.p. injection at 24 hr before TBI at 6.5, 7.5, and 8.5 Gy. Only results of 7.5 and 8.5 Gy TBI are reported here (FIG. 6) because 6.5 Gy did not cause significant mortality. The results showed that (a) The survival rates from both 7.5 and 8.5 Gy of TBI for mice treated with UTS were greatly increased, (b) the rates were drug-dose dependent, and (c) the average body wt of surviving mice pretreated with UTS started to recover from around Day 20. These observations indicate that UTS-1401 is effective as a radioprotector for male NIH Swiss mice against TBI of both 7.5 and 8.5 Gy.

For NIH Swiss Female Mice

It appeared that NIH Swiss female mice are more resistant to TBI and TBI of 6.5 Gy and 7.5 Gy did not results in significant deaths. Only 8.5 Gy results are summarized here. Pretreatment of UTS-1401 (at 50, 100, and 150 mg/kg) all showed significant radioprotective effects and reduced the mortality caused by the 8.5 Gy TBI. However, the radioprotective effects were essentially the same for all 3 doses of UTS-1401 indicating that the optimal dose may be around 50 mg/kg. The results of the 24-hr pretreatment of UTS-1401 at 24 hr before the TBI at 8.5 Gy are shown in FIG. 7.

Figure 6:
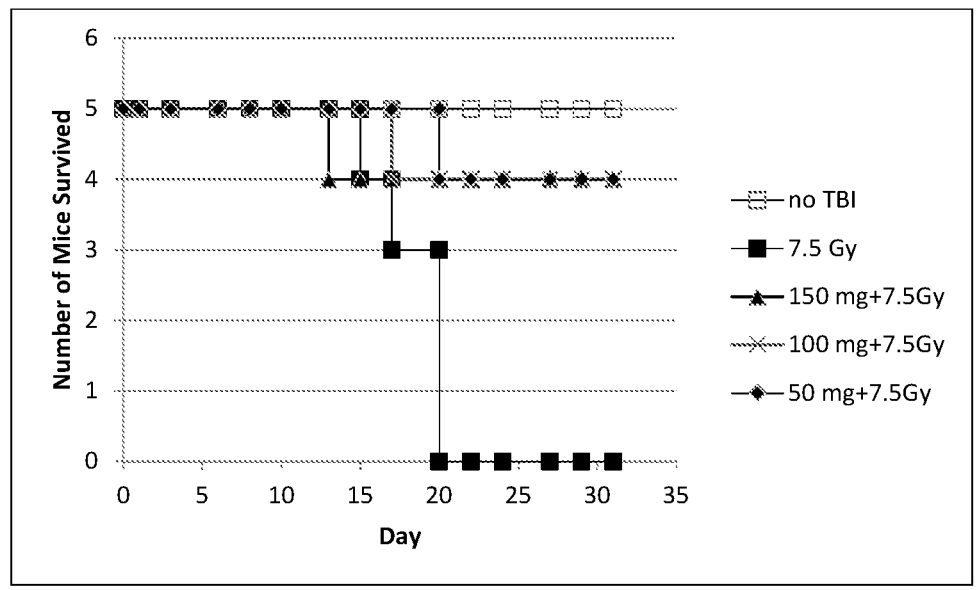
FIG. 6 is a graph of the effect of UTS-1401 (at 100 mg/kg 24 hr before TBI) on TBI induced mortality in NIH-Swiss mice.

FIG. 6 is a graph of the effect of UTS-1401 on TBI induced mortality in NIH-Swiss mice administered at 100 mg/kg determined according to Example 5.

Figure 7:
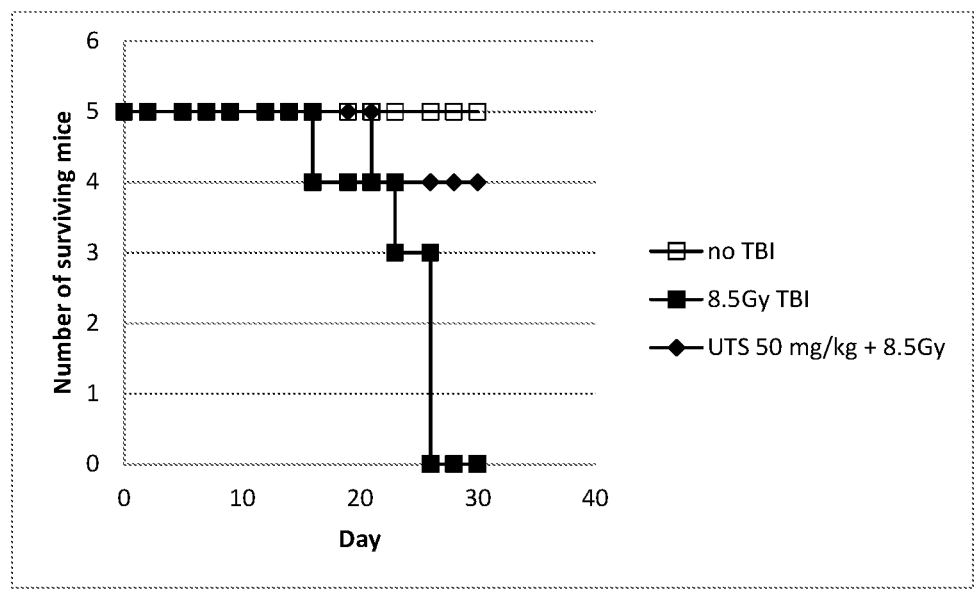
FIG. 7 is a graph of the effect of UTS-1401 (at 150 mg/kg 24 hr before TBI) on TBI induced mortality in NIH-Swiss female mice.

FIG. 7 is a graph of the effect of UTS-1401 on TBI induced mortality in NIH-Swiss mice administered at 150 mg/kg determined according to Example 5.

Example 6

Protection Against Doxorubicin-Induced Damage on Cardiomyocytes by UTS-1401 In Vitro Briefly, myocardiocytes H9C2 were cultured in high glucose DMEM with 10% bovine calf serum and 10,000 cells per well of cardiomyocytes were treated by DOX with and without the 30 min pretreatment of UTS-1401. The survival rates were assayed by MTT assay 3 days later. The results showed that UTS-1401 protected cardiomyocytes significantly indicating that UTS-1401 is a potential cardioprotective agent for DOX-induced toxicity.

Figure 8:
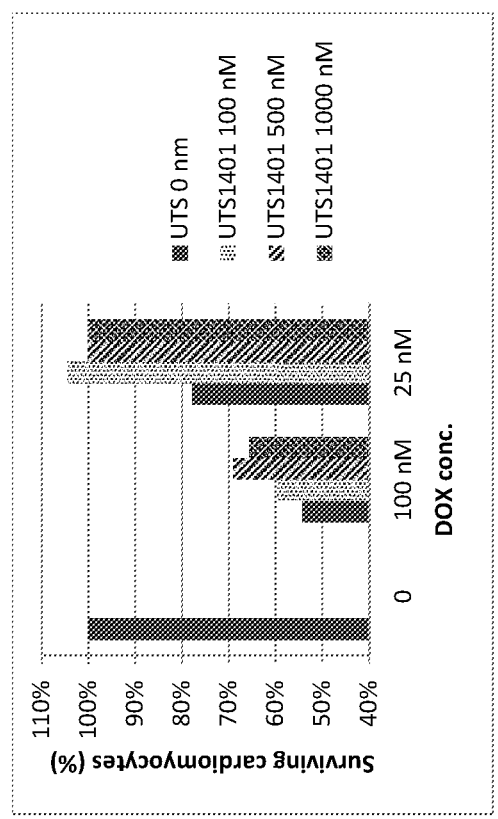
FIG. 8 is a graph showing protection of UTS-1401 on H9C2 cardiomyocytes against DOX-induced damage.

FIG. 8 is a graph showing protection of UTS-1401 on H9C2 cardiomyocytes against DOX-induced determined according to Example 6.

Example 7

Solubility Determination of UTS-14 Compounds
Procedure

The solubility of UTS-14 compounds were determined by accurately weighing predetermined amount of the compound of interest, adding small amount of solvent (e.g., 0.2 mL), shaking, letting the solution sit at rm temp, and observing daily. If the compound was not dissolved, more solvent was added and the solution was watched again after one day. This procedure was continued until the compound was completely dissolved, after which the solubility was calculated. Some results are shown below:
UTS-1401 solubility in water: ca. 9.5 mg/mL
UTS-1401 solubility in saline at 37° C.: 12 mg/ml
UTS-1402 solubility in water: ca. 16 mg/mL
UTS-1403 solubility in water: ca. 9.1 mg/mL
UTS-1403 in Hank's Balanced Salt Solution (HBSS): ca. 15.8 mg/mL in HBSS

Example 8

Making the Sodium Salt of UTS-1403
Procedure

Weigh 205.2 mg of UTS-1403 (mw 205.2) into 100 mL of 0.01N NaOH (eq to 40 mg of NaOH).
Mix well until all of UTS-1403 dissolved.
Filter off any particulates.
Concentrate slowly to crystallize to make the sodium salt of UTS-1403.

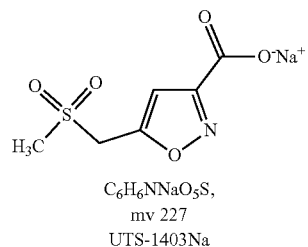

$C_6H_6NNaO_5S$,
mv 227
UTS-1403Na

Various salts of each of UTS-1401, UTS-1402 and UTS-1403 could be produced by those skilled in the art in a similar manner.

As can be appreciated, the present invention discloses and provides a series of new compounds and methods of reducing injuries caused by radiation or chemicals. Although the description above contains many specificities, these should not be construed as limiting the scope of the invention but as merely providing the illustrations of some of the presently preferred embodiments of this invention. Thus the scope of this invention should be determined by the appended claims and their legal equivalents, rather than by the specificities or examples given.

The invention claimed is:

1. A method of protecting healthy living tissues/organs of a subject from radiation-induced injuries, which injuries are induced by localized radiotherapy applied to a cancer patient for treatment of cancer, said method comprising administration of a pharmaceutically acceptable salt of a compound of formula (I)

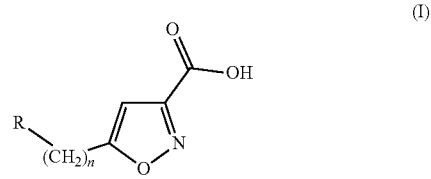

(I)

wherein n is 1 or 2, and, independently, R is Br, Cl, H—O, $H_3C$—S,

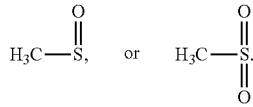

2. A method of protecting healthy living tissues or organs of a subject from chemical-induced injuries, which injuries are induced by chemotherapy, said method comprising administration of a pharmaceutically acceptable salt of a compound of formula (I)

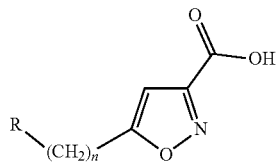

wherein n is 1 or 2, and, independently, R is Br, Cl, H—O, $H_3C$—S,

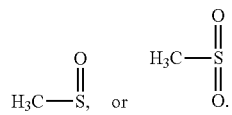

3. A method of protecting healthy living tissues/organs of a subject from radiation-induced injuries, which injuries are induced by total-body irradiation or localized radiotherapy of a cancer patient subject for therapeutic purpose or applied to a subject exposed to non-medical radiation resulting from terrorism, nuclear war or accidental exposure, said method comprising administration of a pharmaceutically acceptable salt of a compound of formula (I)

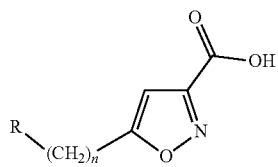

wherein n is 1 or 2, and, independently, R is Br, Cl, H—O, $H_3C$—S,

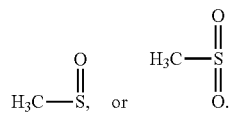

4. A method of protecting healthy living tissues/organs of a subject from radiation-induced or chemical-induced injuries which method comprises administration of a compound of formula (I)

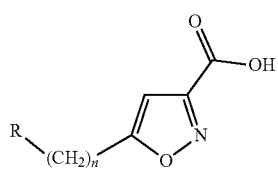

or pharmaceutically acceptable salt thereof, wherein n is 1 or 2, and, independently, R is Br, Cl, H—O or

5. The method according to claim 4, wherein the radiation-induced injuries are induced by total-body irradiation or localized radiotherapy.

6. The method according to claim 4, wherein the radiation-induced injuries are induced by localized radiotherapy applied to a cancer patient for treatment of cancer.

7. The method according to claim 5 wherein the radiation-induced injuries are induced by total-body irradiation that is applied to a cancer patient for therapeutic purpose or applied to a subject exposed to non-medical radiation resulting from terrorism, nuclear war or accidental exposure.

8. The method according to claim 4, wherein the chemical-induced injuries are induced by chemotherapy.

9. The method according to claim 4, wherein the chemical-induced injuries are induced by accidental chemical exposure.

10. A method of protecting healthy living tissues/organs of a subject from radiation-induced or chemical-induced injuries which method comprises administration of a compound of formula (I)

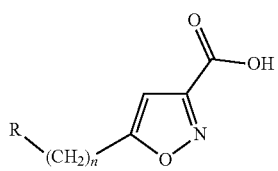

or pharmaceutically acceptable salt thereof, wherein n is 2 and, independently, R is Br, Cl, H—O, $H_3C$—S,

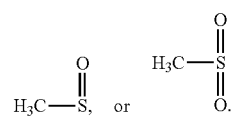

11. The method according to claim 10, wherein the radiation-induced injuries are induced by total-body irradiation or localized radiotherapy.

12. The method according to claim 10, wherein the radiation-induced injuries are induced by localized radiotherapy applied to a cancer patient for treatment of cancer.

13. The method according to claim 11, wherein said total-body irradiation is applied to a cancer patient for therapeutic purpose or applied to a subject exposed to non-medical radiation resulting from terrorism, nuclear war or accidental exposure.

14. The method according to claim 10, wherein the chemical-induced injuries are induced by chemotherapy.

15. The method according to claim 10, wherein the chemical-induced injuries are induced by accidental chemical exposure.

* * * * *